United States Patent [19]

Mezrich et al.

[11] 4,131,025

[45] Dec. 26, 1978

[54] PULSE-ECHO ULTRASONIC-IMAGING DISPLAY SYSTEM

[75] Inventors: Reuben S. Mezrich, Rocky Hill; Jeremiah Y. Avins, Kendall Park, both of N.J.

[73] Assignee: RCA Corporation, New York, N.Y.

[21] Appl. No.: 766,526

[22] Filed: Feb. 7, 1977

[30] Foreign Application Priority Data

Jul. 26, 1976 [GB] United Kingdom ............... 31114/76

[51] Int. Cl.² ............................................. G01N 29/00
[52] U.S. Cl. ........................................ 73/606; 73/642
[58] Field of Search ............ 73/67.5 R, 67.7, 67.8 R, 73/67.8 S, 67.9, 71.5 US, 606, 607, 625, 614, 632, 626, 641, 642, 629; 340/5 MP, 5 H, 8 FT, 8 L; 128/2 V, 2.052

[56] References Cited

U.S. PATENT DOCUMENTS

| 2,833,999 | 5/1958 | Howry | 73/642 |
|---|---|---|---|
| 3,886,490 | 5/1975 | Green | 340/5 MP |
| 3,895,525 | 7/1975 | Eichelberger et al. | 340/5 MP |
| 3,918,024 | 11/1975 | Macovski | 340/5 MP |
| 3,918,297 | 11/1975 | Rocha | 73/607 |
| 3,937,066 | 2/1976 | Green et al. | 340/5 MP |
| 3,958,559 | 5/1976 | Glenn et al. | 73/642 |
| 4,001,766 | 1/1977 | Hurwirtz | 340/5 H |
| 4,016,750 | 4/1977 | Green | 73/629 |

Primary Examiner—Stephen A. Kreitman
Attorney, Agent, or Firm—H. Christoffersen; Samuel Cohen; George J. Seligsohn

[57] ABSTRACT

An improvement to a pulse-echo ultrasonic-imaging system employing an acoustic focusing device occupying a fixed aperture to both illuminate internal structure of a visually opaque object with a scanning focused beam of ultrasonic energy and for returning a reflected signal portion of the scanning focused beam passed therethrough for detection. The improvement makes it possible to employ a large numerical aperture spherical lens exhibiting aberration as the focusing device by utilizing a corrector plate. The corrector plate causes the lens to image a flat transducer in a flat image field. Were it not for the corrector plate, the lens aberration would provide an undesired curved image field. The improved system is suitable for displaying deep soft tissue of a living human being for a medical diagnostic purpose.

6 Claims, 8 Drawing Figures

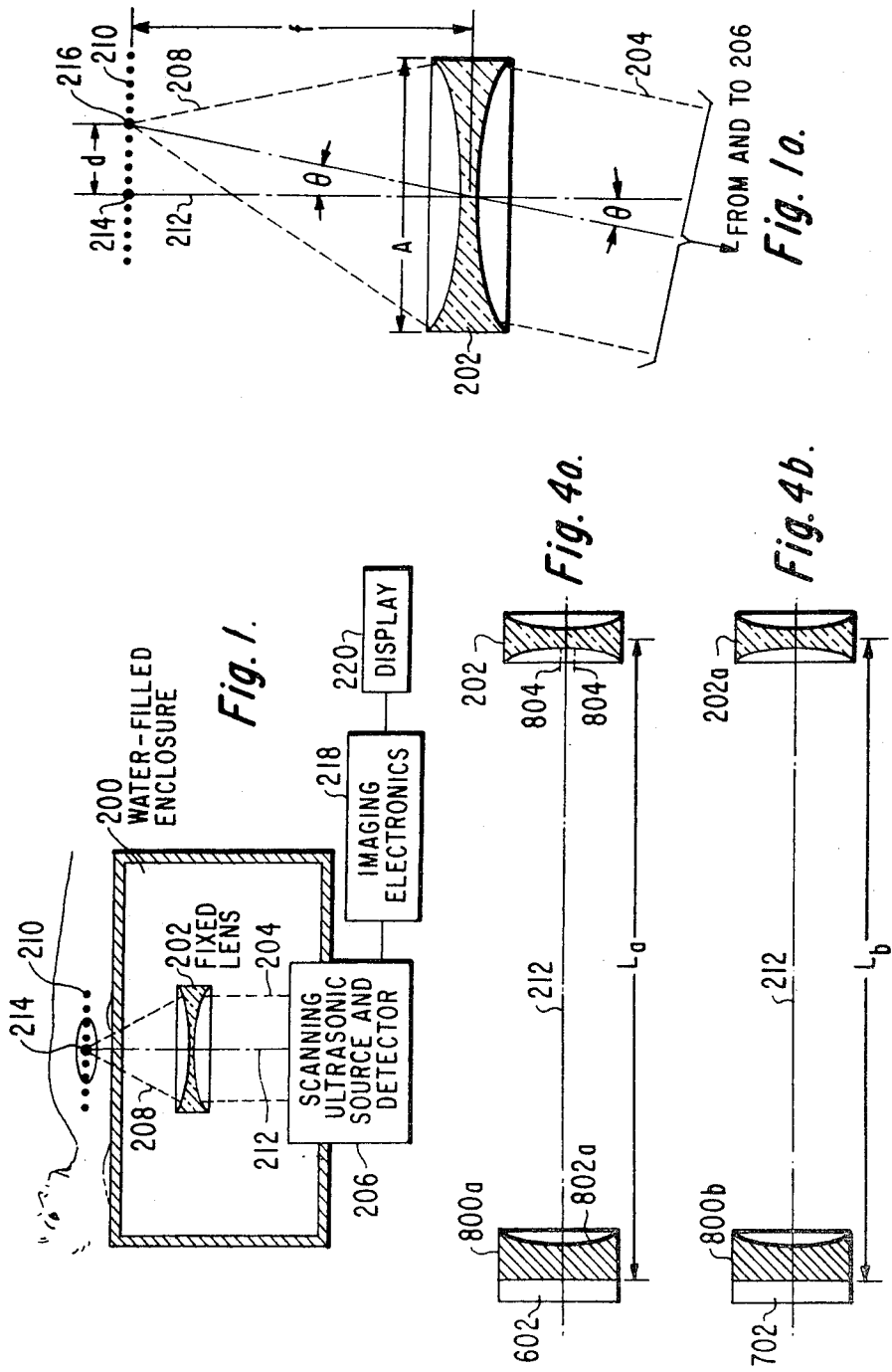

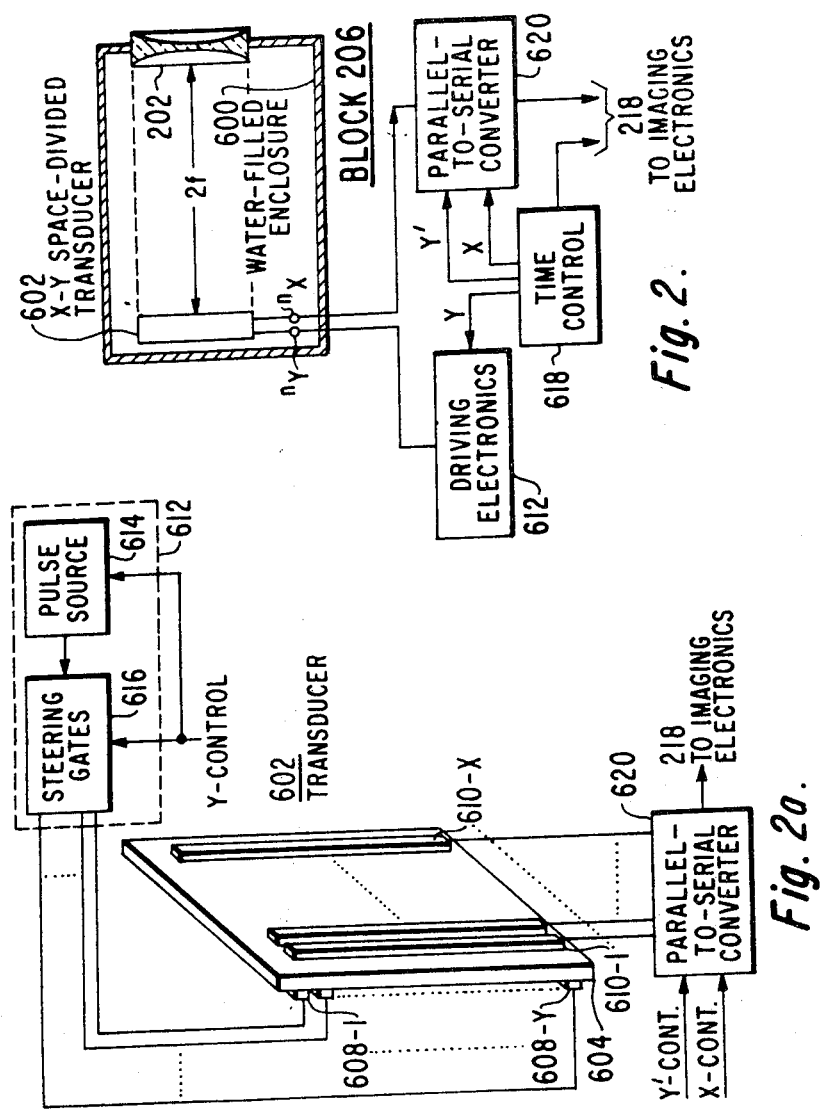

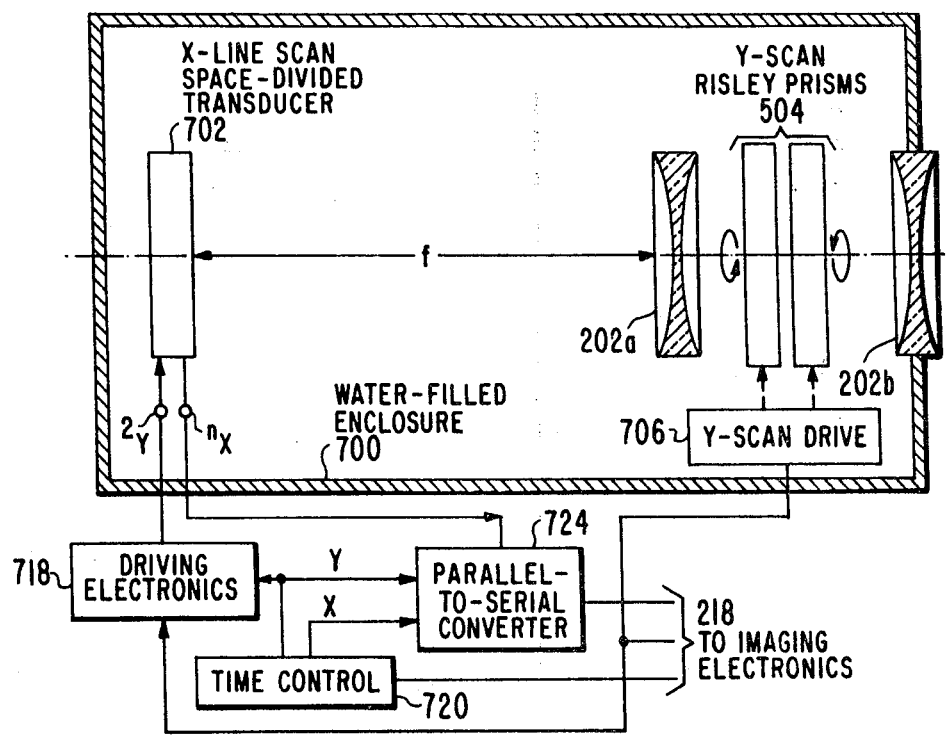
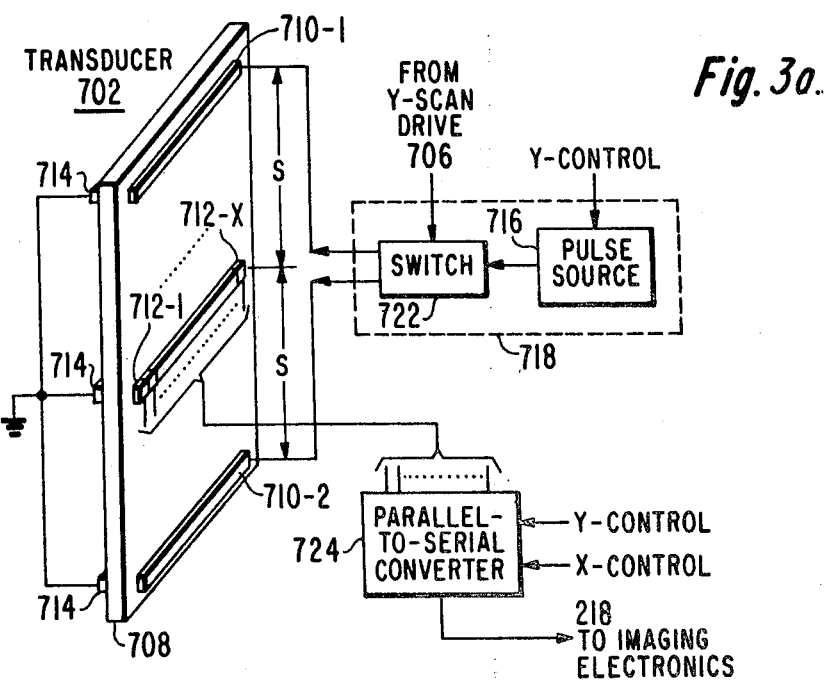

PULSE-ECHO ULTRASONIC-IMAGING DISPLAY SYSTEM

Reference should be made to the following U.S. patent applications, filed concurrently herewith and assigned to the same assignee as the present invention:

Ser. No. 766,564 — Mezrich and Koenig
Ser. No. 766,565 — Mezrich and Anderson
Ser. No. 766,527 — Mezrich
Ser. No. 766,528 — Mezrich and Vilkomerson The aforesaid U.S. patent application Ser. No. 766,564 Mezrich and Koenig describes in detail a number of embodiments of a high resolution pulse-echo ultrasonic-imaging display system employing an acoustic focused device occupying a fixed aperture for both illuminating internal structure of a visually opaque object with a scanning focused beam of ultrasonic energy and for returning a reflected signal portion of the scanning focused beam passed therethrough for detection. The present application is directed to apparatus employing a corrector plate for use when the focusing device is a lens for imaging a flat transducer and the lens exhibits aberrations. Were it not for the corrector plate, the lens aberrations would cause the flat transducer to be imaged in a curved image field.

In the drawings:

FIGS. 1 and 1a generically illustrate the type of pulse-echo ultrasonic-imaging system that may embody the present invention;

FIGS. 2 and 2a illustrate a first species of the scanning ultrasonic source and detector of FIG. 1;

FIGS. 3 and 3a illustrate a second species of the scanning ultrasonic source and detector of FIG. 1; and FIGS. 4a and 4b illustrate the use of a corrector plate for use with each of the aforesaid first and second species, respectively;

FIGS. 1, 1a, 2, 2a, 3, 3a, 4a and 4b of the present case correspond identically with respective FIGS. 2, 2a, 6, 6a, 7, 7a, 8a and 8b of the aforesaid U.S. patent application Ser. No. 766,564.

Referring now to FIGS. 1 and 1a, there is shown a human patient lying on water-filled table 200. Immersed within water-filled table 200 is fixed lens 202, which is illuminated by a substantially plane wavefront beam 204 of ultrasonic energy from scanning ultrasonic source and detector 206 disposed in spaced relationship with fixed lens 202.

The term "fixed" lens, as used herein, means that the effective position of the aperture of lens 202 remains substantially stationary with respect to the human patient lying on water-filled table 200 during an image scan. However, in order to select the particular soft tissue within the human patient to be imaged, the operating distance between lens 202 and the human patient may be adjusted, if desired, prior to an image scan, by either changing the height of the top of water-filled table 200 with respect to lens 202 or by changing the position of lens 202 with respect to the top of water-filled table 200, without departing from the above definition of "fixed" lens. Further, since the mere rotation of a circularly symmetrical lens about its own axis has no effect at all on the position of the lens aperture or the way the lens acts on ultrasonic energy transferred therethrough, such mere rotation of the lens about its own axis is to be construed as to be within the above definition of the term "fixed" lens. Fixed lens 202 transfers the ultrasonic energy in plane wavefront beam 204 incident thereon into converging beam 208, which focuses at a small spot of focal plane 210 of lens 202 (located within the body of the human patient).

FIG. 1 shows plane-wavefront illuminating beam 204 of ultrasonic energy at a point in its scan where its direction of travel is parallel to acoustic axis 212 of fixed lens 202. In this case, ultrasonic energy converging beam 208 emerging from fixed lens 202 focuses at a spot centered at focal point 214 in focal plane 210 of lens 202. However, as shown in FIG. 1a, when plane wavefront illuminating beam 204 is at a point in its scan where its direction of travel is angularly displaced by angle $\theta$ from acoustic axis 212 of lens 202, converging beam 208 emerging from lens 202 focuses at a spot centered at point 216 in focal plane 210 of lens 202. As shown in FIG. 1a, point 216 is linearly displaced by a distance d from focal point 214. As is known in the optical art, the relationship between the distance d and the angular displacement $\theta$ is given by the following equation:

$$d = f\theta, \quad (1)$$

where f is the focal distance of lens 202, as shown in FIG. 1a, and the maximum value of $\theta$ is sufficiently small (as is the case) to be substantially equal to radians to tan $\theta$.

It will be noted from equation 1 that the value of d varies linearly with $\theta$. Further, as the value $\theta$ varies during a scan, the position of the point, such as point 216, to which beam 208 converges remains in focal plane 210. This ensures a substantially flat-field image (neglecting the effect of any lens aberrations).

Referring now to FIGS. 2 and 2a, there is shown a space-divided embodiment of scanning ultrasonic source and detector 206 for providing real-time scanning of the target area. Lens 202 is incorporated into the front wall of water-filled enclosure 600. Immersed in water-filled enclosure 600 is X-Y space-divided transducer 602. Transducer 602 is preferably situated at a distance from lens 202 equal to twice its focal length (2f), as indicated in FIG. 2, so that points on transducer 602 are imaged with unity magnification on a target area plane situated at a distance beyond lens 202 also equal to 2f. Similarly, points in the target area will be imaged with unity magnification at transducer 602. As shown in FIG. 2a, transducer 602 comprises piezoelectric plate 604 having a first set of driving line-section electrodes 608-1 ... 608-y on the left surface thereof and a second set of sensing line-section electrodes 610-1 ... 610-x on the right face thereof. As shown, the second set of electrodes is orthogonally oriented with respect to the first set of electrodes to thereby define (x · y) cross points therebetween. Each of these cross points corresponds to a sampling point of the target area. If, as has been assumed, x and y both have a value of 100, the total number of sampling points in the scan of the target area is 10,000.

Driving electronics 612 for energizing transducer 602 comprises pulse source 614 and steering gate 616. More specifically, under the control of Y signals from time control 618, steering gate 616 operates as a commutator to selectively supply successive exploratory pulses in sequence to each of driving electrodes 608-1 ... 608-y, while simultaneously grounding all the non-selected remaining ones of this first set of electrodes. At the time an exploratory pulse is applied to driving electrodes 608-1 ... 608-y, sensing electrodes 610-1 ... 610-x are also grounded. This results in a narrow (e.g. 1 mm.) line beam of ultrasonic energy consisting of the energy launched from each of the cross-points of the then-selected one of driving electrodes 608-1 ... 608-y.

Because each sampling point of the target area is imaged at a corresponding cross-point of the transducer in the arrangement of block 206 shown in FIGS. 2 and 2a, the round-trip travel time between the transmission of an exploratory pulse and the receipt of an echo from the target area in response thereto is twice that of the previously-discussed embodiments of block 206. More specficially, if the target area is situated ten inches beyond lens 202 (i.e. $2f=10$ inches), as has been assumed, the total distance between transducer 602 and the target area is 20 inches. Therefore, the round trip travel time is in the order of 660 $\mu$s (assuming a velocity of 1500 m/s for the ultrasonic energy in the propagating medium.

Y control signals are applied to pulse source 614 in steering gates 616 at the beginning of a Y repetition period equal to or slightly greater than the round-trip travel time (660 $\mu$s) to cause each respective driving electrode 608-1 ... 608-y to launch an exploratory pulse of ultrasonic energy in consecutive order at substantially 600 $\mu$s intervals.

Parallel-to-serial converter 620, which includes a set of x storage elements, a set of input gates under the control of Y' signals from time control 618 for applying the signals sensed by the sensing electrodes 610-1 ... 610-x to the corresponding storage elements at or near the end of each Y (660 $\mu$s) period, and a steer-out circuit under the control of Y- signals from time control 618 for sequentially reading out all the stored signals on the set of storage elements during the following Y period to thereby apply a serial stream of x (e.g. 100) sample point signals to imaging electronics 218 during that Y period. Time control 618 also supplies scan sync signals to imaging electronics 218. Thus, the scan of the entire target area takes (y+1) Y periods or, in the assumed example, 66.66 ms. This is a real-time frame rate of 15 scans of the target area per second.

At the end of any Y period, while parallel-to-serial converter 620 is sampling the echoes returned from the target area in response to the exploratory pulse transmitted from a particular one of driving line-section electrodes at the beginning of that Y period, it may be desirable for steering gate 616 to momentarily disconnect electrodes 608-1 ... 608-y (i.e. allow electrode 608-1 ... 608-y to float), in order to reduce the effective shunting parasitic load impedance between sensing electrodes 610-1 ... 610-x and ground. This shunting load impedance tends to reduce the effective sensitivity and raise the effective signal-to-noise ratio of the sensed signals forwarded by sensing electrodes 610-1 ... 610-x to the storage elements of parallel-to-serial-converter 620. In any event, all other things being equal, the greater the number x-y cross-points, the greater is the effect of the shunting lead impedance.

FIGS. 3 and 3a show an embodiment of scanning ultrasonic source and detector 206, which operationally is the functional equivalent of the embodiment shown in FIGS. 2 and 2a, but which inherently exhibits a much lower parasitic shunting load impedance.

Referring to FIG. 3, immersed in water-filled enclosure 700 are X-line-scan space-divided transducer 702 and Y-scan Risley prisms 704 coupled to Y-scan drive 706. Sample points of the target area are imaged at corresponding points of transducer 702 by a lens system composed of two spaced lenses 202a and 202b, situated, as shown, on either side of Y-scan Risley prisms 704. This imaging results from the fact that lens 202b, which is incorporated in the front wall of water-filled enclosure 700, has its focal plane situated in coincidence with the target area, and transducer 702 is located in the focal plane of lens 202a. The use of a two-lens system to provide imaging of the sample points of the target area on transducer 702 is to be preferred in the arrangement of FIG. 3 to the single lens approach used in FIG. 2 because the two-lens approach ensures less distortion because the Y-scan Risley prisms are illuminated with paraxial plane-wave acoustic energy, rather than spherical wave energy from a linearly scanned point source.

Referring now to FIG. 3a, transducer 702 comprises piezoelectric plate 708 having two driving line-section electrodes 710-1 and 710-2 mounted on the right face thereof. Halfway between driving line-section electrode 710-1 and 710-2, at a distance "s" from each, is a linear array of individual sensing electrodes 712-1 ... 712-x. Mounted on the left face of piezoelectric plate 708, in corresponding relationship with each of driving line-section electrodes 710-1 and 710-2 and the linear array of sensing electrodes 712-1 ... 712-x are grounded line-section electrodes 714, as shown. Pulse source 716 of driving electronics 718, in response to Y control signals from time control 720, applies a series of exploratory pulses to a selected one of driving electrodes 710-1 and 710-2 through switch 722 at a repetition rate which is substantially equal to the round trip travel time between the transmission of an exploratory pulse and a receipt of an echo from the target area response thereto (e.g. 660 $\mu$m). Switch 722 selects the one of the driving electrodes 710-1 and 710-2 which an exploratory pulse is forwarded in response to a control signal from Y-scan drive 706 applied thereto.

Y-scan Risley prisms 704 are continuously rotating during the time an exploratory-pulse is traveling toward the target and during the time that an echo therefrom is traveling back toward transducer 702. Therefore, an echo responsive to an exploratory pulse launched from a selected one of driving electrodes 710-1 and 710-2 does not return to that selected driving electrode, but is incrementally deflected in the Y direction by a given distance which is determined by the speed of rotation of Y-scan Risley prisms 704 and the round-trip travel time to the target area. The spacing distance between the linear array of sensing electrode 712-1 ... 712-x and either one of the driving electrode 710-1 and 710-2 is chosen to be equal to this given distance. Furthermore, during a first half of each cycle of Y-scan Risley prisms 704, a beam of acoustic energy passing therethrough is deflected in the Y-direction from top-to-bottom. However, during the remaining half of each cycle of location of Y-scan Risley prisms 704, a beam of acoustic energy passing therethrough is deflected in the Y-direction from bottom-to-top. The control signal applied to switch 722 from Y-scan drive 706 causes exploratory pulses to be forwarded to driving electrode 710-1 and driving electrode 710-2 to be grounded during the half-cycle of rotation of Y-scan Risley prisms 704 when the acoustic beam is being deflected from top-to-bottom. Similarly, exploratory pulses are applied to driving electrode 710-2 and driving electrode 710-1 is grounded by switch 722 during those half-cycles of Risley prisms 704 during which the acoustic beam is deflected from bottom-to-top. In either case, returning echoes from the target area are incident on the linear-array of sensing electrode 712-1 ... 712-x.

Assuming that the cycle period of Y-scan Risley prisms 704 is not exactly equal to an even integral multiple of the repetition period of the exploratory pulses, a different set of X-lines of the target area will be sampled during consecutive half-cycles of rotation of Risley prisms 704. That is, an inter-laced raster scan of the target area is achieved.

Parallel-to-serial converter 724, which is structurally and functionally identical to parallel-to-serial converter 620, described above, the end of each Y period (i.e. exploratory pulse repetition period) samples in parallel and stores all the line of target area echo signals then being received by sensing electrode 712-1 ... 712-x, and then converts the stored signals into a corresponding serial stream during the following Y periods.

Ideally, lens 202 in FIG. 2 images flat transducer 602 in a flat image plane and lenses 202a and 202b in FIG. 3 images flat transducer 702 in a flat image plane. However, as is known in the optical art, conventional spherical lenses exhibit various forms of aberration. Further, the magnitude of these aberrations tends to increase for large aperture lenses, particularly when the object (transducer) occupies a relatively wide field (which is the case in FIGS. 2 and 3).

An especially troublesome aberration to which the arrangements of FIGS. 2 and 3 are subject is the imaging of respective flat transducers 602 and 702 in a concavely curved image plane. One way of overcoming this problem is to provide lens 202 of FIG. 2 and lenses 202a and 202b of FIG. 3 with appropriate complex curvatures derived by computer-controlled ray-tracing techniques, known in the art. However, machining large-aperture acoustic lenses with such complex curvatures is both difficult and expensive. A simpler and less expensive solution to this problem is shown in FIGS. 4a and 4b.

Referring to FIG. 4a, corrector plate 800a is disposed, as shown, between transducer 602 and lens 202 in substantial contact with the front surface of transducer 602. Transducer 602 has a relatively high acoustic impedance relative to that of water, the propagating medium. Therefore, corrector plate 800a should be composed of a material exhibiting an acoustic impedance intermediate that of transducer 602 and water. Preferably, the acoustic impedance of corrector plate 800a should be close to the geometric mean between that of transducer 602 and water to provide optimum impedance matching for the ultrasonic wave energy. In practice, corrector plate 800a may be made out of the same material, such as a plastic like polystyrene or methylmethacralate, as that of acoustic lens 202. However, preferably, corrector plate 800a should be composed of a metal, such as aluminum, which exhibits an acoustic impedance to the propagating ultrasonic waves closer to that required for optimum impedance matching than the acoustic impedance exhibited by a plastic.

Corrector plate 800a has a concave front surface 802a, so that it operates as an acoustic condensing lens for (1) retaining an increased portion of the ultrasonic wave energy emitted by transducer 602 within the aperture of lens 202 to thereby increase the ultrasonic wave energy efficiency of the system and, more important, (2) concentrating a very large proportion of the total ultrasonic wave energy illuminating large aperture lens 202 in the small aperture central region 804 thereof surrounding axis 212. Therefore, the large aperture of lens 202 provides the required high resolution capabilities with which the acoustic wave energy is focused in the image plane, while, at the same time, the concentration of the ultrasonic wave energy by corrector plate 800a within small aperture region 804 of lens 202 minimizes any undesired curvature of the image plane.

Where cost is no object, the curvature of surface 802a and/or the surfaces of lens 202 can be tailored by ray-tracing techniques to substantially eliminate one or more of the aberrations normally produced by a large aperture lens. However, when both lens 202 and corrector plate 800a have inexpensively produced spherical surfaces, the undesired curvature of the image plane still can be substantially eliminated by providing the condensing lens formed by corrector plate 800a with a focal length substantially equal to distance $L_a$ between the principal plane of corrector plate 800a and that of acoustic lens 202.

The arrangement of FIG. 2 employs a single lens 202 while the arrangement in FIG. 3 employs two spaced lenses 202a and 202b. As shown in FIG. 4b, the condenser lens formed by corrector plate 800b associated with transducer 702 of FIG. 3 has a focal length equal to the distance $L_b$ between the principal plane of corrector plate 800b and the closer acoustic lens 202a of FIG. 3, to thereby concentrate the acoustic wave energy illuminating lens 202a in the central region thereof surrounding axis 212. In all other respects, the arrangement shown in FIG. 4b is substantially identical to that shown in FIG. 4a, described above.

What is claimed is:

1. In apparatus for use in an ultrasonic pulse-echo system capable of displaying an image of certain internal structure of a visually opaque object being scanned with ultrasonic wave energy, said apparatus including an acoustic focusing device occupying a given aperture which aperture remains substantially fixed in position with respect to said object while said object is being scanned, and ultrasonic beam forming means including transducer means generating successive pulses of ultrasonic wave energy and beam scanning means for illuminating said certain internal structure through said focusing device with a scanning focused beam of said pulsed ultrasonic wave energy, said transducer means being situated remotely from both said focusing device and from said internal structure for receiving and detecting a signal portion of said focused beam reflected from said certain internal structure and returned through said focusing device to said transducer means after a time delay proportional to the distance between said remotely situated transducer means and internal structure; the improvement:

wherein said transducer means includes a substantially flat transducer plate situated with respect to said focusing device in an image plane of said object, wherein said focusing device includes at least one large aperture acoustic lens exhibiting abberation which by itself would cause said flat transducer plate to be imaged in a given curved image field, and wherein said beam forming means further includes a corrector plate situated between said transducer plate and said acoustic lens in substantially direct contact with said transducer plate, said corrector plate being made of a material exhibiting that predetermined normalized index of refraction with respect to its surroundings for said ultrasonic waves which is less than unity and having that predetermined varying thickness over its cross-section which makes said corrector plate substantially compensate for said abberation, whereby the presence of said corrector plate results in said flat transducer plate to be imaged in a flat image field.

2. The apparatus defined in claim 1, wherein said transducer plate, said corrector plate and said acoustic lens are all immersed in an ultrasonic wave propagating medium and said transducer plate and said acoustic lens are separated from each other by a given distance, and wherein said predetermined index of refraction and predetermined varying thickness of said corrector plate have respective values that result in the ultrasonic wave energy from said transducer plate passing through said corrector plate being converged toward the center of said acoustic lens.

3. The apparatus defined in claim 2, wherein said acoustic lens has a spherical surface and said predetermined varying thickness of said corrector plate defines a concave spherical surface of given radius facing said acoustic lens, and wherein said given radius of said concave spherical surface of said corrector plate provides said corrector plate with a focal length substantially equal to said given distance.

4. The apparatus defined in claim 2, wherein said transducer plate exhibits an acoustic impedance substantially different from that exhibited by said propagating medium, and wherein said corrector plate material exhibits an acoustic impedence intermediate that of said transducer plate and that of said propagating mediam.

5. The apparatus defined in claim 4, wherein said corrector plate material is aluminum.

6. The apparatus defined in claim 4, wherein said corrector plate material is a given plastic.

* * * * *

UNITED STATES PATENT AND TRADEMARK OFFICE
CERTIFICATE OF CORRECTION

PATENT NO. : 4,131,025

DATED : December 26, 1978

INVENTOR(S) : Reuben Saul Mezrich et al

It is certified that error appears in the above-identified patent and that said Letters Patent is hereby corrected as shown below:

Column 8, line 14, "mediam" should read --median--

Signed and Sealed this

Twenty-fourth Day of April 1979

[SEAL]

Attest:

RUTH C. MASON
Attesting Officer

DONALD W. BANNER
Commissioner of Patents and Trademarks